US008586331B2

(12) United States Patent
Slagman et al.

(10) Patent No.: US 8,586,331 B2
(45) **Date of Patent: *Nov. 19, 2013**

(54) **PROCESS FOR THE PRODUCTION OF THE *ACTINOBACILLUS PLEUROPNEUMONIAE* TOXIN APXI EMPLOYING A CULTURE MEDIUM COMPRISING CALCIUM-BOROGLUCONATE COMPLEX**

(75) Inventors: Simen-Jan Slagman, Boxmeer (NL); Christian Theodoor Gerardus Smits, Boxmeer (NL); Bayram Bulut, Boxmeer (NL)

(73) Assignee: Intervet International B.V., Boxmeer (NL)

( * ) Notice: Subject to any disclaimer, the term of this patent is extended or adjusted under 35 U.S.C. 154(b) by 137 days.

This patent is subject to a terminal disclaimer.

(21) Appl. No.: 13/131,129

(22) PCT Filed: Nov. 25, 2009

(86) PCT No.: PCT/EP2009/065798

§ 371 (c)(1), (2), (4) Date: May 25, 2011

(87) PCT Pub. No.: WO2010/060917

PCT Pub. Date: Jun. 3, 2010

(65) Prior Publication Data

US 2011/0229935 A1 Sep. 22, 2011

Related U.S. Application Data

(60) Provisional application No. 61/118,770, filed on Dec. 1, 2008.

(30) Foreign Application Priority Data

Nov. 27, 2008 (EP) .................................... 08105881

(51) Int. Cl.
*C12P 21/04* (2006.01)

(52) U.S. Cl.
USPC ........... 435/71.3; 435/6.15; 435/41; 435/70.1

(58) Field of Classification Search
USPC ................................ 435/6.15, 41, 70.1, 71.3
See application file for complete search history.

(56) References Cited

U.S. PATENT DOCUMENTS

| | | | | |
|---|---|---|---|---|
| 6,019,984 | A | 2/2000 | MacInnes et al. | |
| 2011/0229934 | A1* | 9/2011 | Slagman et al. | 435/71.3 |

FOREIGN PATENT DOCUMENTS

| | | |
|---|---|---|
| EP | 0 453 024 | 10/1991 |
| EP | 0 875 574 | 11/1998 |

OTHER PUBLICATIONS

Frey, J., et al., "*Actinobacillus pleuropneumoniae* RTX-toxins: Uniform Designation of Haemolysins, Cytolysins, Pleurotoxin and their Genes", Journal of General Microbiology, (1993) 139(8):1723-1728.

Hsu, Yuan-Man, et al., "Cloning and Characterization of the *Actinobacillus pleuropneumoniae fur* Gene and its Role in Regulatin of ApxI and AfuABC Expression", The Journal of DNA Sequence and Mapping, (Jun. 2003) 14(3):169-181.

Jarma, Erica, et al., "Anaerobiosis, Growth Phase and *Actinobacillus pleuropneumoniae* RTX toxin Production", Microbial Pathogenesis, (2004) 37(1):29-33.

Kennedy, M. and Krouse, D., "Strategies for Improving Fermentation Medium Performance: A Review", Journal of Industrial Microbiology & Biotechnology, (1999) 23:456-475.

MacPherson, Herbert Taylor, et al., "Investigations on the Nature of Calcium Borogluconate", Biochemical Journal, (Jan. 1938) 32(1):76-78.

International Search Report for corresponding PCT/EP2009/065798, mailed Jan. 7, 2010.

* cited by examiner

*Primary Examiner* — Susan Hanley
*Assistant Examiner* — Nghi Nguyen

(57) ABSTRACT

The present invention pertains to a method to produce RTX-toxin Apxl by culturing *Actinobacillus pleuropneumoniae* bacteria in a liquid culturing medium that supports growth of the bacteria, to which medium a calcium salt is added to form calcium ions in the medium, wherein the culturing medium contains borogluconate to form a calcium borogluconate complex in the medium.

8 Claims, No Drawings

PROCESS FOR THE PRODUCTION OF THE *ACTINOBACILLUS PLEUROPNEUMONIAE* TOXIN APXI EMPLOYING A CULTURE MEDIUM COMPRISING CALCIUM-BOROGLUCONATE COMPLEX

CROSS-REFERENCE TO RELATED APPLICATIONS

This application is a national stage entry under 35 U.S.C §371 of PCT/EP2009/065798 filed on Nov. 25, 2009, which claims priority of EP application No. 08105881.0, filed on Nov. 27, 2008, and under 35 U.S.C §119(e), to provisional application U.S. Ser. No. 61/118,770, filed Dec. 1, 2008. The content of PCT/EP2009/065798 is hereby incorporated by reference in its entirety.

The present invention pertains to a method to produce RTX-toxin ApxI by culturing *Actinobacillus pleuropneumoniae* bacteria in a culturing medium that supports growth of the bacteria, to which medium a calcium salt is added to form calcium ions in the medium.

Porcine pleuropneumoniae, a major respiratory disease in pigs, is spread out worldwide and causes severe economic losses to the pig industry due to peracute deaths, treatment of acutely sick pigs and the delays in marketing of chronically infected animals. The etiological agent is *Actinobacillus pleuropneumoniae*. It is transmitted primarily by directcontact between animals, and the resulting infection produces a clinical course varying from peracute to chronic. The disease is primarily an infection of the respiratory tract having the clinical signs of high fever, severe respiratory distress, coughing and anorexia. The onset of the disease is rapid and morbidity and mortality are high. One of the ways to control *Actinobacillus pleuropneumoniae* (from now on also called "APP") infections is by vaccination programs. Bacterins have in the passed been used in such programs but were known for their serious side effects. Nowadays subunit vaccines based on the toxins of APP are commonly used.

APP produces so-called RTX-toxins (RTX stands for repeat-in-toxin). It is the presence of these RTX-toxins that highly contributes to the pathogenic character of this bacterium. The RTX-toxins have been extensively reviewed in the past and described in literature. As is commonly known, not all APP serotypes produce all RTX-toxins. For example, serotypes 1, 5, 9 and 11 produce ApxI and ApxII. Serotypes 2, 3, 4, 6 and 8 produce ApxII and AxpII. Serotype 10 produces ApxI only and serotypes 7 and 12 produce ApxII only. Current commercially available vaccines against APP are based on the toxins ApxI, ApxII and ApxIII. Fairly recently it has been found that all APP serotypes produce a fourth RTX toxin, now called ApxIV (see EP 0 875 574).

It is commonly known how to produce the RTX-toxin ApxI by culturing *Actinobacillus pleuropneumoniae* in a culturing medium to which a calcium salt (i.e. a chemical compound, based on an acid, formed by replacing all or part of the hydrogen ions of the acid with one or more calcium ions) is added. In particular, EP 0 453 024 already describes such a method (see "Example 2", paragraph 2 "Purification and characterisation of hemolysin", subparagraph "Methods"). Note that ApxI used to be referred to as "HLY" (see Frey et al. in "J Gen Microbiol. 1993 August; 139(8): 1723-8"). From this EP patent it is known to add a calcium compound ($CaCl_2$) to the medium. Indeed, in Microbiol Pathogenesis 37 (2004) 29-33 it is stated that transcriptional activity of the ApxI operon is enhanced by addition of calcium to the growth medium. This way, high levels of ApxI can be provided for. The medium should support the growth of APP bacteria. It is commonly known how to constitute a medium that supports growth of bacteria. Classical culture media were originally developed by Eagle, Ham and others in the 1950's and 60's. They found that a medium which fulfils the basic needs for growth should comprise inorganic salts, a nitrogen source (for example in the form of nitrogen containing compounds such as peptides or proteins), a carbon source and vitamins. The media are advantageously buffered to prevent them from becoming either too acidic or too alkaline. Within this basic recipe, many different constitutions are available. For example, one could opt for animal derived components to provide the amino acids, but one could also choose for chemically defined amino acids. For the other compounds also numerous variations are possible. Indeed, to constitute a medium that supports growth of bacteria is relatively simple. However, optimisation of growth and/or metabolite production can take some development time, in particular when a medium is preferred that is free of serum or other animal derived components. Strategies for improving fermentation medium performance however are commonly known in the art and elaborately described in literature (see for example a review article by Kennedy and Krouse in the Journal of Industrial Microbiology & Biotechnology (1999) 23, 456-475). Such optimisation forms part of the routine experiments within a fermentation lab. In case of cultivation of APP, NAD (nicotinamide adenine dinucleotide) inherently forms part of the medium since APP is NAD dependent. Without NAD, the medium will not support growth of the *Actinobacillus pleuropneumoniae* bacteria and can thus not be considered as a liquid medium for supporting growth of APP in the sense of the present application and the appended claims. Media for supporting growth of bacteria, or components to constitute such media, are commercially available from various companies such as Sigma Aldrich, Quest International, Oxoid, Becton Dickinson, Pharmacia, VGD Inc, Mediatech, Invitrogen, Marcor, Irvin Scientific etc.

Although prior art methods suffice in obtaining an economically relevant yield of the ApxI toxin, applicant recognised that there might be a possibility for improvement. During fermentation namely, the medium becomes opaque. It was applicants merit to realise that this may be due to a precipitation of a (or more) calcium salts. APP namely produces carbon dioxide which in the medium results in carbonate ions. Calcium carbonate is a salt with a particularly low solubility. As a consequence several problems may occur. Firstly, it is believed that precipitation renders the calcium ions involved, out of reach for the APP bacteria. Secondly, precipitated calcium salts give rise to problems in down stream processing. In particular filters tend to become silted up. Therefore, applicant added various complexing agents to the medium to see whether or not they could prevent precipitation of the salt. Indeed, for example by adding EDTA, the medium may remain more or less transparent. However, ApxI production yield is negatively influenced by using such complexing agents. The hypothesis therefore might be wrong or incomplete. Still, there is a continuous desire to improve ApxI production.

Surprisingly, it has been found that when borogluconate (e.g. in the form of 2,3-dihydroxy-3-[2-hydroxy-5-(hydroxymethyl)-1,3,2-dioxaborolan-4-yl]propanoate; see also Herbert Taylor MacPherson and James Stewart of the Moredun Institute in the Biochemical Journal;" Investigations on the nature of calcium borogluconate", received 16 Nov. 1937) is used to complex the calcium ions, one can produce ApxI at a high level when compared with prior art methods that use no (added) complexing agents or rely on other complexing agents. Apparently, by using this particular complexing agent, such that the medium contains the complex calcium borogluconate (e.g. available as D-Gluconic acid, cyclic 4,5-ester with boric acid, calcium salt 2:1) substantial precipitation of the calcium ions with other negative ions can be prevented, while at the same time the calcium ions are still available for enhancing the transcriptional activity of the ApxI operon of *Actinobacillus pleuropneumoniae*. Apparently the calcium ions stay trapped in the salt complex, wherein the "trapping" bonds on the one hand are strong enough to prevent the calcium ions from forming a precipitate with for example carbonate or other negative ions, but on the other hand do not prevent the bacterium itself to use the calcium ions as if they were in free solution (i.e. complexed by water molecules only). Apparently, borogluconate exactly fulfills the critical balance that is needed for the production of ApxI by APP.

In an embodiment the borogluconate concentration is less than 60 mmol/l. Above this concentration it appears that the ApxI production decreases to low levels. Although still usable, it is preferred that the concentration stays below this figure. Even further preferred are concentrations between 25 and 45 mmol/l, in particularly 40 mmol/l which appears to be optimal for several media.

Although not essential for the present invention, the medium may be free of animal components. A disadvantage of many prior art methods is that they rely on the use of media containing animal derived components such as Columbia broth. Other animal derived components mentioned in the prior art are for example Columbia Broth Modified or Brain Heart Infusion broth. As is commonly known, the use of animal components has some severe drawbacks. First of all, the chemical composition may vary considerably between production lots. Also, supplements of animal origin may be contaminated with infectious agents. A major fear is the presence of prions causing TSE in humans or animals. One could simply opt for a medium that is free of animal components (often referred to as an "ACF"-medium). "Animal component" in this sense means any component that is present as such in an animal (for example, blood or a protein) or derived from such a component (for example modified serum derived from the blood, or amino acids derived from the protein). Applicant however found that the ApxI production efficiency is far lower when such ACF media are used when compared to media containing animal derived components, even when the calcium concentration is at a sufficient level. Without being bound to theory, it may be that with the use of serum, the problem with calcium salt precipitation is not so severe due to the presence of agents that form soluble complexes of the calcium ions. In any case, when borogluconate is used to complex the calcium ions, significant ApxI yield increase can also be obtained in these media.

In another embodiment the calcium salt is calcium borogluconate. Although one could for example still use calcium chloride as the calcium source and add a borogluconate salt for complexing the calcium ions, it is preferred that the calcium is added as the borogluconate salt. This way, there is no need to await equilibrium between the various physical reactions (precipitation, dissolving, complex-deformation, complex-formation) that take place in the medium. This saves time and thus is economically favourable.

In yet another embodiment during culturing air is passed through the liquid medium, which air contains carbon dioxide above atmospheric level. Surprisingly it has been seen that carbon dioxide improves the ApxI production rate even further. It is noted that it is generally known to use an increased carbon dioxide level during the culturing of colonies of bacteria on plates (see e.g. U.S. Pat. No. 6,019,984: EXAMPLES "Bacterial Strains and Growth Conditions"). However, this concerns the culturing of colonies of bacteria, which bacteria are then used for inoculating fermentors. At this stage, the production of RTX toxins is not relevant. Even stronger, it is generally understood (see e.g. Microbial Pathogenesis 37 (2004) 29-33) that the maximum Apx production takes place at high cell densities in fermentors, thus at the end of the exponential growth phase. At this stage, carbon dioxide is understood to be no longer relevant as a stimulating factor. Therefore, it has not been tried before to increase Apx production by using increased carbon dioxide levels. In particular, applicant recognized that when the air contains 5% carbondioxide v/v (volume pure carbon dioxide over volume of plain air), ApxI production is at a very high level. It is noted that many techniques to pass air through the medium can be used in this embodiment, usually though via a device that lets air bubbles escape somewhere in the medium (i.e. under the surface of the medium). "Air" in the context of the present invention means a gaseous medium comprising one or more gaseous components that are normally present in atmospheric air such as oxygen, nitrogen, carbon dioxide, helium, neon, argon, xenon, radon etc.

The invention will be further explained by using the following non-limiting examples.

Materials En Methods

Bacterial Strain and Media

The studies were performed using an ApxI producing *Actinobacillus pleuropneumnoiae* strain, serotype 10, hereafter called APP 10. In all cases, a working seed of this strain was reconstituted using Columbia Blood AgarBASE (BAB) plates (available from Becton, Dickinson USA). Liquid media used were either Columbia broth (available from Becton, Dickinson USA) kept at a pH of 7.3 using NaOH and acetic acid, or an animal component free medium (called "ACF medium"). The latter medium contains $MgSO_4$ (0.75 g/l), cysteine.HCl (0.1 g/l), $FeCl_3$ (0.1 g/l), $NaN0_3$ (0.1 g/l), KCl (0.1 g/l), tracer elements (e.g. 2.5 ml of solution SL-10 as mentioned in the Handbook of Microbiological Media, 3rd edition, Ronald Atlas, CRC Press, 2004), 50% glucose solution (10 ml) and a 10 mM amino acids solution (containing all 20 amino acids, except tryptophan), HEPES buffer (6 g/l; e.g. available from Sigma Aldrich) and yeast extract (10 g/l; e.g. available from Becton Dickinson).

These media were used in precultures and in fermentations. Nicotinamide Adenine Dinucleotide (0.01%) and calcium (various concentrations) were used in precultures and fermentations. All media were sterilized by 0.22 μm filtration. Prior to utilization in fermentations, the media were heated at 85° C. for one minute.

Cultivation

A working seed of the APP 10 strain was plated out on a Columbia BAB plate and incubated during approximately 24 hours at 37° C. Several colonies were picked to inoculate a 500 mL bottle containing 75 ml Columbia broth. The bottle was incubated during approximately 6 hours at 37° C. under agitation to form a preculture. With this preculture several fermentations were carried out. Some of these took place in 500 ml bottles. In that case, 75 ml of the medium was inoculated with 1 mL of the preculture. The bottles were incubated at 37° C. under agitation. Alternatively, cultivation took place in SIXFORS fermenters (Infors AG, Switzerland) containing approximately 400 mL culture medium, whereto 20 mL of the preculture was added as inoculum. Cultivation temperature is also 37° C.

Analyses

Cell growth was determined by measuring the optical density (OD) at 660 nm. The ApxI antigen concentration was measured by routine ELISA determination.

Results

The first experiment was conducted to determine whether or not the calcium, despite being complexed with borogluconaat is still available for the APP bacteria. This experiment was carried out in the bottles as described here-above. The results are indicated here-beneath in table 1.

TABLE 1

| Medium | ApxI antigen (U/mL) |
|---|---|
| Columbia broth, no Ca added | 0 |
| Columbia broth, 25 mM Ca-borogluconate added | 7 |

As the data in Table 1 indicate, a good ApxI yield can be provided for when complexing the calcium ions with borogluconate. An important advantage of this complexing is that calcium salt precipitations do no longer significantly influence down stream processing.

The second experiment was conducted to see what the effect is of borogluconate in the animal component free medium. To this end, we compared the addition of 20 mM $CaCl_2$ with the addition of 20 mM Ca-borogluconate. The results are depicted in Table 2.

TABLE 2

| Medium | ApxI antigen (U/mL) |
|---|---|
| ACF, 20 mM $CaCl_2$ added | 1 |
| ACF, 20 mM Ca-borogluconate added | 24 |

Two results are obtained. Firstly, it is clear that obtaining sufficient quantities of ApxI in an ACF medium is difficult when using calcium chloride, even when normal calcium levels are created. When complexing the calcium with borogluconate a high ApxI yield can be obtained. Comparable results can be obtained in other media. We conducted such an experiment in a medium that contained no iron chloride nor magnesium sulphate ("ACF-alt") but otherwise was the same as the ACF medium as described here-above. Again, significantly increased levels were obtained when complexing the calcium with borogluconate.

A third experiment was conducted to study the influence of borogluconate concentration. We used three different concentrations, namely 20, 40 and 60 mM calciumborogluconate. The results are depicted in Table 3.

TABLE 3

| Medium | ApxI antigen (U/mL) |
|---|---|
| ACF, 20 mM Ca-borogluconate added | 4 |
| ACF, 40 mM Ca-borogluconate added | 31 |
| ACF, 60 mM Ca-borogluconate added | 1 |

As becomes clear from Table 3, a concentration of around 40 mM appears to be ideal.

In a fourth experiment, we studied the effect of increased carbon dioxide levels for the ApxI production yield. For this, we used the ACF-alt medium as described here-above and increased the natriumnitrate level to 0.5 g/l. The borogluconate concentration was varied between 40, 50 and 70 mM. The higher concentration of $CO_2$ was achieved by maintaining a constant airflow in the fermentor of 1 vvm (=volume gas per volume medium per minute) for an air/$CO_2$ 95/5 v/v mixture. Experiments were conducted in a SIXFORS fermentor as described here-above. The results are depicted in Table 4.

TABLE 4

| Medium | ELISA ApxI antigen (U/mL) |
|---|---|
| ACF-alt, 40 mM Ca-borogluconate added, 5% $CO_2$ | 520 |
| ACF-alt, 50 mM Ca-borogluconate added, 5% $CO_2$ | 357 |
| ACF-alt, 70 mM Ca-borogluconate added, 5% $CO_2$ | 222 |

From the results it can be concluded that carbon dioxide has a positive influence on ApxI production yield: even at a concentration of 70 mM calciumborogluconate acceptable levels of ApxI can be produced. Again, 40 mM appears to be an optimal concentration.

Conclusion

Applicant found that in a liquid culturing medium that supports growth of APP bacteria, borogluconate can provide the critical balance between the prevention of precipitation of calcium ions with negatively charged ions on the one hand, and keeping the calcium ions available to stimulate *Actinobacillus pleuropneumoniae* to produce ApxI on the other hand. This can be used advantageously in any *Actinobacillus pleuropneumoniae* culturing medium containing negative ions that form a precipitate with calcium ions.

Indeed, depending on the medium chosen and optimization of its constituents, the APP bacteria themselves will produce higher or lower levels of ApxI. But since the shielding action of the borogluconate will work independent of the actual production speed of the bacteria themselves, this solution can be successfully applied for all media, in particular since all media inherently contain carbonate ions, which are ions that can form a precipitate with calcium ions.

The invention claimed is:

1. A method to produce Repeat-In-Toxin (RTX-toxin) ApxI comprising culturing *Actinobacillus pleuropneumoniae* bacteria in a culturing medium that supports growth of the bacteria, to which medium a calcium salt is added to form calcium ions in the medium, characterised in that the culturing medium contains borogluconate to form a calcium borogluconate complex in the medium.

2. The method according to claim 1, characterised in that the borogluconate concentration is less than 60 mmol/l.

3. The method according to claim 2, characterised in that the concentration is between 25 and 45 mmol/l.

4. The method according to claim 1 characterised in that the calcium salt is calcium borogluconate.

5. The method according to claim 2, characterised in that the calcium salt is calcium borogluconate.

6. The method according to claim 3, characterised in that the calcium salt is calcium borogluconate.

7. The method according to claim 3, characterised in that the concentration is 40 mmol/l.

8. The method according to claim 6, characterised in that the concentration is 40 mmol/l.

* * * * *